(12) United States Patent
Dutt

(10) Patent No.: US 11,000,139 B1
(45) Date of Patent: May 11, 2021

(54) NECK PILLOW

(71) Applicant: Alice Marianne R. Dutt, Akron, OH (US)

(72) Inventor: Alice Marianne R. Dutt, Akron, OH (US)

( * ) Notice: Subject to any disclaimer, the term of this patent is extended or adjusted under 35 U.S.C. 154(b) by 28 days.

(21) Appl. No.: 16/551,840

(22) Filed: Aug. 27, 2019

(51) Int. Cl.
| | |
|---|---|
| A47G 9/10 | (2006.01) |
| A47C 16/00 | (2006.01) |
| A61F 5/00 | (2006.01) |
| A61G 7/07 | (2006.01) |
| A61G 15/12 | (2006.01) |
| A61G 5/12 | (2006.01) |
| A47C 20/02 | (2006.01) |
| A61G 13/12 | (2006.01) |

(52) U.S. Cl.
CPC ............ *A47G 9/1081* (2013.01); *A47C 16/00* (2013.01); *A47G 9/10* (2013.01); *A47G 9/1027* (2013.01); *A47C 20/02* (2013.01); *A61F 5/00* (2013.01); *A61G 5/121* (2016.11); *A61G 7/07* (2013.01); *A61G 13/121* (2013.01); *A61G 15/12* (2013.01)

(58) Field of Classification Search
CPC ......... A47C 16/00; A47C 20/00; A47C 20/02; A47C 7/383; A47G 9/10; A47G 9/1027; A47G 9/1081; A47G 9/1072; A47G 9/109; A47G 9/1009; A47G 9/02; A47G 9/0253; A47G 2009/1018; A61G 5/12; A61G 5/121; A61G 7/07; A61G 7/072; A61G 7/1084; A61G 13/121; A61G 15/12; A61G 15/125; A61G 2203/18; A61F 13/00; A61F 5/00
See application file for complete search history.

(56) References Cited

U.S. PATENT DOCUMENTS

| | | | | | |
|---|---|---|---|---|---|
| 3,008,464 | A | * | 11/1961 | Atkins | A61F 5/055 601/39 |
| 4,617,691 | A | * | 10/1986 | Monti | A47C 7/383 128/DIG. 23 |
| 4,776,049 | A | * | 10/1988 | Perron | A47C 7/383 297/393 |
| 4,903,711 | A | * | 2/1990 | Gunther | A61F 5/00 128/874 |
| 5,029,577 | A | * | 7/1991 | Sarkozi | A61F 5/055 602/18 |
| 5,211,623 | A | * | 5/1993 | Sarkozi | A61F 5/055 128/DIG. 23 |
| 6,058,517 | A | * | 5/2000 | Hartunian | A41D 13/0512 2/468 |
| 6,219,865 | B1 | * | 4/2001 | Stokesbary | A47G 9/10 297/392 |

(Continued)

*Primary Examiner* — Robert G Santos
*Assistant Examiner* — Rahib T Zaman

(57) ABSTRACT

The neck pillow comprises a pillow body, a gap, and a plurality of fasteners. The pillow body may be adapted to be worn around a neck of a user and to limit movement of the head relative to the rest of the body. The pillow body may comprise a core and an outer cover. The shape of the pillow body may be an annulus that is three-dimensional. The pillow body may comprise a central aperture that may be adapted for the neck to pass through. The gap may permit the pillow body may to open while donning the pillow body. The plurality of fasteners may hold the gap closed during use. The neck pillow may further comprise a back support, which may be a downward projection from the bottom surface of the pillow body.

14 Claims, 4 Drawing Sheets

(56) References Cited

U.S. PATENT DOCUMENTS

| | | | |
|---|---|---|---|
| 6,457,195 B1* | 10/2002 | Holste | A47C 7/383 5/636 |
| 6,641,221 B1* | 11/2003 | Kastlunger | A47C 7/383 297/392 |
| 6,786,554 B1* | 9/2004 | Zahiri | B60N 2/882 297/393 |
| 6,926,686 B2* | 8/2005 | Cheatham | A61F 5/055 128/DIG. 23 |
| D766,015 S | 9/2016 | Thelonious | |
| 9,554,662 B2* | 1/2017 | Law | A47G 9/1081 |
| 9,968,197 B2* | 5/2018 | Wong | A47C 7/383 |
| 10,076,190 B2* | 9/2018 | Atkinson | A47C 7/383 |
| D834,350 S | 11/2018 | Zou | |
| 2012/0011655 A1* | 1/2012 | Rojas | A47C 7/383 5/636 |
| 2014/0000036 A1* | 1/2014 | Cohen | A47C 27/081 5/639 |
| 2014/0310877 A1* | 10/2014 | Sternlight | A47C 31/00 5/639 |
| 2014/0359943 A1* | 12/2014 | Casta-Baez | A47G 9/109 5/636 |
| 2015/0059098 A1* | 3/2015 | Jung | D05B 93/00 5/636 |
| 2016/0007777 A1* | 1/2016 | Gang | B60N 2/882 5/639 |
| 2016/0257228 A1* | 9/2016 | Lederer | A47C 7/383 |
| 2017/0000273 A1* | 1/2017 | Mitchell | A47C 7/383 |
| 2018/0289183 A1 | 10/2018 | Karl | |
| 2018/0310731 A1* | 11/2018 | Staton | A47G 9/0253 |
| 2019/0038053 A1* | 2/2019 | Brantingham | A47C 7/383 |

* cited by examiner

NECK PILLOW

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of pillows, more specifically, a neck pillow.

SUMMARY OF INVENTION

The neck pillow comprises a pillow body, a gap, and a plurality of fasteners. The pillow body may be adapted to be worn around a neck of a user and to limit movement of the head relative to the rest of the body. The pillow body may comprise a core and an outer cover. The shape of the pillow body may be an annulus that is three-dimensional. The pillow body may comprise a central aperture that may be adapted for the neck to pass through. The gap may permit the pillow body may to open while donning the pillow body. The plurality of fasteners may hold the gap closed during use. The neck pillow may further comprise a back support, which may be a downward projection from the bottom surface of the pillow body.

An object of the invention is to provide an annular pillow that may be worn around the neck of a user.

Another object of the invention is to provide a non-linear gap where the pillow may open for donning.

A further object of the invention is to provide a plurality of fasteners to prevent the gap from opening during use of the pillow.

Yet another object of the invention is to provide a back support project downwards from the bottom of the pillow.

These together with additional objects, features and advantages of the neck pillow will be readily apparent to those of ordinary skill in the art upon reading the following detailed description of the presently preferred, but nonetheless illustrative, embodiments when taken in conjunction with the accompanying drawings.

In this respect, before explaining the current embodiments of the neck pillow in detail, it is to be understood that the neck pillow is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the neck pillow.

It is therefore important that the claims be regarded as including such equivalent construction insofar as they do not depart from the spirit and scope of the neck pillow. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
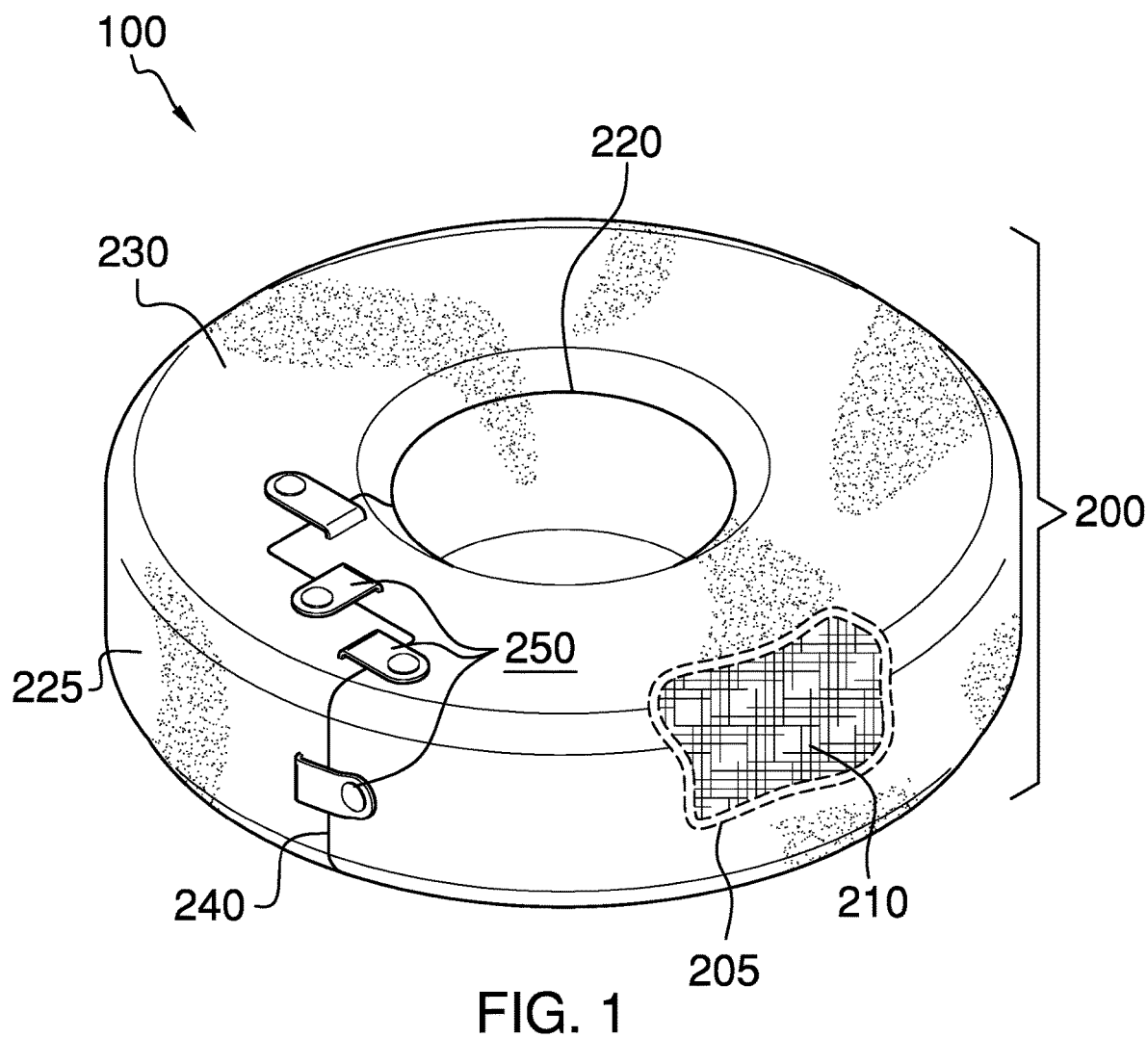
FIG. 1 is a perspective view of an embodiment of the disclosure.
Figure 2:
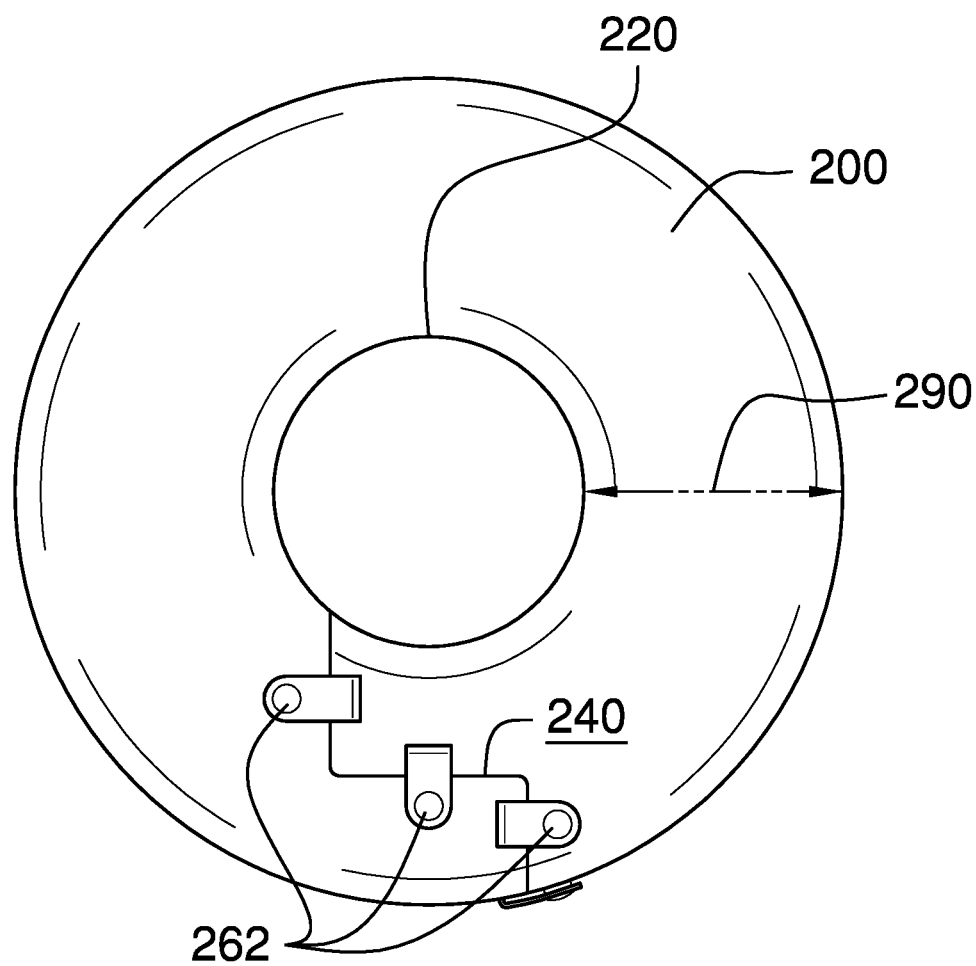
FIG. 2 is a top view of an embodiment of the disclosure.
Figure 3:
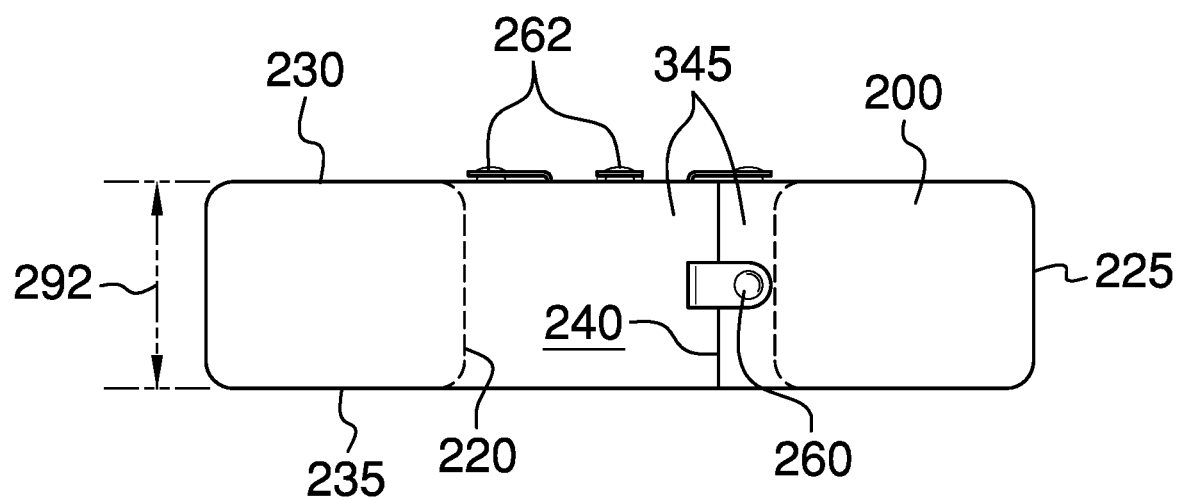
FIG. 3 is a rear view of an embodiment of the disclosure.
Figure 4:
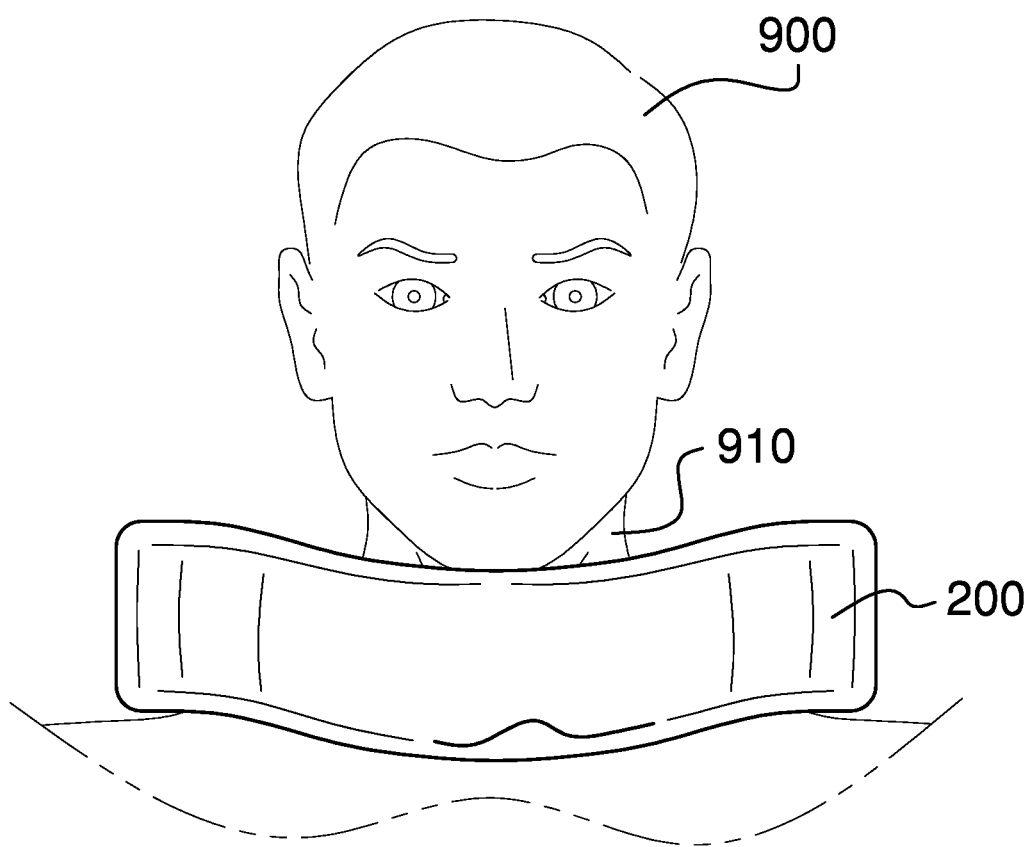
FIG. 4 is a front in-use view of an embodiment of the disclosure.
Figure 5:
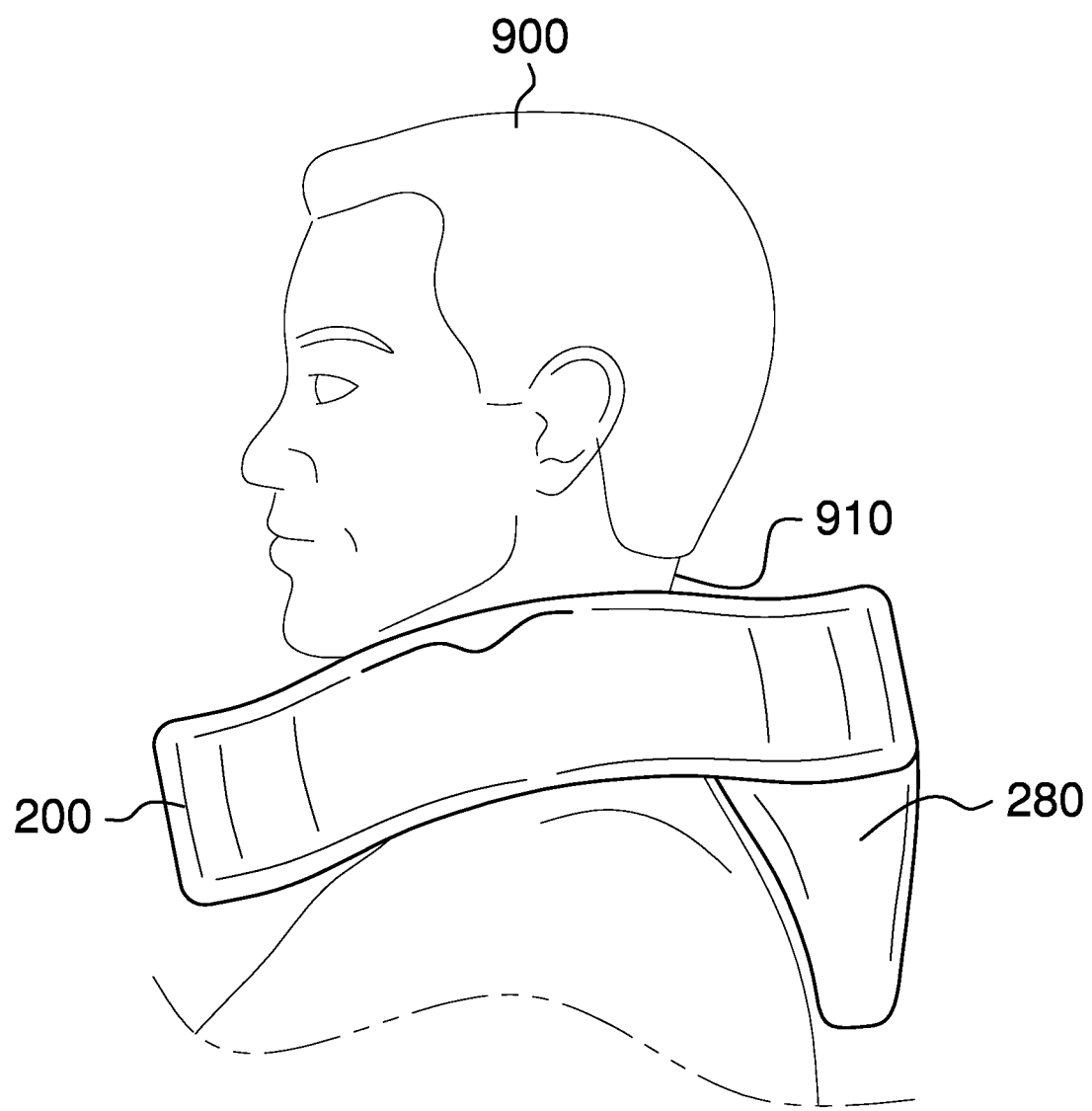
FIG. 5 is a side view of an alternative embodiment of the disclosure illustrating the back support.

Detailed reference will now be made to a first potential embodiment of the disclosure, which is illustrated in FIGS. 1 through 5.

The neck pillow 100 (hereinafter invention) comprises a pillow body 200, a gap 240, and a plurality of fasteners 250. The pillow body 200 may be adapted to be worn around a neck 910 of a user 900. The pillow body 200 may comprise the gap 240 such that the pillow body 200 may be opened while donning the pillow body 200. The plurality of fasteners 250 may hold the gap 240 closed during use.

The pillow body 200 may comprise a core 210 and an outer cover 205. The pillow body 200 may be a flexible or semi-rigid support adapted to be worn around the neck 910 and to limit movement of the head relative to the rest of the body. The shape of the pillow body 200 may be determined by the outer cover 205 and the core 210. The shape of the pillow body 200 may be an annulus that is three-dimensional. The pillow body 200 may comprise a central aperture 220. The central aperture 220 may pass through the pillow body 200 from top to bottom. The central aperture 220 may be adapted for the neck 910 to pass through.

The core 210 may fill the outer cover 205 to prevent the outer cover 205 from collapsing. The core 210 may be made from natural or synthetic material. As non-limiting examples, the core 210 may be made from monolithic or shredded foam, fiberfill, cotton, wool, kapok, down and feather, or combinations thereof.

The outer cover 205 may be a flexible covering for the core 210. The outer cover 205 may be made from natural or synthetic material. As non-limiting examples, the outer cover 205 may be made from cotton, linen, silk, polyester, polycotton, nylon, bamboo, rayon, or combinations thereof.

In some embodiments, the pillow body 200 may be inflatable. As a non-limiting example, the outer cover 205 may be vinyl and the core 210 may be pressurized air. In some embodiments, the outer cover 205 may be removable from the core 210 such that the outer cover 205 may be laundered.

The gap 240 may be a rift in the pillow body 200. The pillow body 200 may be adapted to be pulled from opposing sides to create an opening at the gap 240 such that the pillow body 200 may be slid onto the neck 910. The profile of the gap 240 when viewed from above may be non-linear such that the gap 240 creates a non-planar rift in the pillow body 200. The non-linear profile of the gap 240 may create a longer boundary along which the plurality of fasteners 250 may be placed. Specifically, as viewed from above the gap 240 may be Z-shaped and may extend from the central aperture 220 to a sidewall 225.

The plurality of fasteners 250 may comprise one or more side fasteners 260 and one or more top fasteners 262. The plurality of fasteners 250 may couple ends of the gap 245 to prevent the pillow body 200 from opening. The one or more side fasteners 260 may be coupled to the sidewall 225 of the pillow body 200. In some embodiments, the one or more side fasteners 260 may be hook and loop fasteners or snap fasteners. The one or more top fasteners 262 may be coupled to a top surface 230 of the pillow body 200. In some embodiments, the one or more top fasteners 262 may be hook and loop fasteners or snap fasteners.

The invention 100 may further comprise a back support 280. The back support 280 may comprise a downward projection from a bottom surface 235 of the pillow body 200. The back support 280 may be adapted to be wedged between the user 900 and an object behind the user for stabilization of the pillow body 200. The back support 280 may couple to the pillow body 200 at any position on the bottom surface 235 of the pillow body 200 that is not below the gap 240. The back support 280 may be tapered such that the back support 280 is narrower at the bottom of the back support 280 than it is at the top of the back support 280.

In some embodiments, a width of the annulus 290 may be 5 inches+/−1 inch. In some embodiments, a height of the annulus 292 may be 4 inches+/−1 inch. In some embodiments, the circumference of the central aperture 220 may be between 12 inches and 22 inches.

In use, the pillow body 200 may be opened by disconnecting the plurality of fasteners 250 and pulling the ends of the gap 245 apart. The pillow body 200 may be placed onto the neck 910 by passing the ends of the gap 245 on either side of the neck 910 such that the neck 910 is in the central aperture 220, allowing the ends of the gap 245 to come together, and reconnecting the plurality of fasteners 250. The pillow body 200 may be removed by reversing the process. In embodiments with the back support 280, the pillow body 200 should be rotated such that the back support 280 is behind the user 900.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" refers to top and "lower" refers to the bottom. As a non-limiting example, the upper end of a vertical shaft is the top end of the vertical shaft.

As used in this disclosure, an "aperture" is an opening in a surface. Aperture may be synonymous with hole, slit, crack, gap, slot, or opening.

As used in this disclosure, a "boundary" refers to a line segment or surface that forms a some or all of the perimeter of a first space and some or all of the perimeter of a second space. Stated less formally, the boundary forms at least part of the delineation between the first space and the second space. When identifying a boundary within this disclosure, a first space may be said to "be bounded" by one or more additional spaces.

As used herein, the words "couple", "couples", "coupled" or "coupling", refer to connecting, either directly or indirectly, and does not necessarily imply a mechanical connection.

As used in this disclosure, "flexible" refers to an object or material which will deform when a force is applied to it, which will not return to its original shape when the deforming force is removed, and which may not retain the deformed shape caused by the deforming force.

As used herein, "front" indicates the side of an object that is closest to a forward direction of travel under normal use of the object or the side or part of an object that normally presents itself to view or that is normally used first. "Rear" or "back" refers to the side that is opposite the front.

As used in this disclosure, a "hook and loop fastener" is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface.

As used in this disclosure, "resilient" or "semi-rigid" refer to an object or material which will deform when a force is applied to it and which will return to its original shape when the deforming force is removed.

As used in this disclosure, a "snap" is a fastener that comprises a male component and a female component. The snap is engaged by pressing the male component into the female component.

As used herein, "Z shaped" refers to the appearance of an element where a first line segment or plane is offset from and parallel to a second line segment or plane and the first line segment or plane is coupled to the second line segment or plane by a third line segment or plane such that the first line segment or plane and the second line segment or plane are on opposing sides of the third line segment or plane. The third line segment or plate may be perpendicular to the first and second line segments or plates but is not required to be perpendicular. The resulting profile of the first, second, and third line segments or planes may resemble the letter 'Z'.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A neck pillow comprising: a pillow body, a gap, and a plurality of fasteners; wherein the pillow body is adapted to be worn around a neck of a user; wherein the pillow body comprises the gap such that the pillow body is opened while donning the pillow body; wherein the plurality of fasteners hold the gap closed during use; wherein the pillow body comprises a core and an outer cover; wherein the pillow body is a flexible or semi-rigid support adapted to be worn around the neck and to limit movement of the head relative to the rest of the body; wherein the shape of the pillow body is determined by the outer cover and the core; wherein the shape of the pillow body is an annulus that is three-dimensional; wherein the pillow body comprises a central aperture; wherein the central aperture passes through the pillow body from top to bottom; wherein the central aperture is adapted for the neck to pass through; wherein the core fills the outer cover to prevent the outer cover from collapsing; wherein the gap is a rift in the pillow body; wherein the pillow body is adapted to be pulled from opposing sides to create an opening at the gap such that the pillow body slides onto the neck; wherein the profile of the gap when viewed from above is non-linear such that the gap creates a non-planar rift in the pillow body; wherein the non-linear profile of the gap creates a longer boundary along which the plurality of fasteners is placed.

2. The neck pillow according to claim 1 wherein the outer cover is made from cotton, linen, silk, polyester, polycotton, nylon, bamboo, rayon, or combinations thereof.

3. The neck pillow according to claim 1 wherein the pillow body is inflatable.

4. The neck pillow according to claim 3 wherein the outer cover is vinyl and the core is pressurized air.

5. The neck pillow according to claim 1 wherein the outer cover is removable from the core such that the outer cover is laundered.

6. The neck pillow according to claim 1 wherein the plurality of fasteners comprise one or more side fasteners and one or more top fasteners; wherein the plurality of fasteners couple ends of the gap to prevent the pillow body from opening.

7. The neck pillow according to claim 6 wherein the one or more side fasteners are coupled to the sidewall of the pillow body.

8. The neck pillow according to claim 7 wherein the one or more side fasteners are hook and loop fasteners or snap fasteners.

9. The neck pillow according to claim 7 wherein the one or more top fasteners are coupled to a top surface of the pillow body.

10. The neck pillow according to claim 9 wherein the one or more top fasteners are hook and loop fasteners or snap fasteners.

11. The neck pillow according to claim 9 wherein the neck pillow further comprises a back support; wherein the back support comprises a downward projection from a bottom surface of the pillow body; wherein the back support is adapted to be wedged between the user and an object behind the user for stabilization of the pillow body; wherein the back support couples to the pillow body at any position on the bottom surface of the pillow body that is not below the gap; wherein the back support is tapered such that the back support is narrower at the bottom of the back support than it is at the top of the back support.

12. The neck pillow according to claim 9 wherein a width of the annulus is 5 inches+/−1 inch.

13. The neck pillow according to claim 9 wherein a height of the annulus is 4 inches+/−1 inch.

14. The neck pillow according to claim 9 wherein the circumference of the central aperture is between 12 inches and 22 inches.

* * * * *